US009125577B2

(12) United States Patent
Sameni et al.

(10) Patent No.: US 9,125,577 B2
(45) Date of Patent: Sep. 8, 2015

(54) EXTRACTION OF FETAL CARDIAC SIGNALS

(71) Applicants:Massachusetts Institute of Technology, Cambridge, MA (US); Institut Polytechnique de Grenoble, Grenoble Cedex (FR); Université Joseph Fourrier, Gronoble Cedex 9 (FR)

(72) Inventors: Reza Sameni, Shiraz (IR); Christian Jutten, Proveysieux (FR); Mohammad B. Shamsollahi, Tehran (IR); Gari D. Clifford, Oxford (GB)

(73) Assignees: MASSACHUSETTS INSTITUTE OF TECHNOLOGY, Cambridge, MA (US); INSTITUT POLYTECHNIQUE DE GRENOBLE, Grenoble Cedex (FR); UNIVERSITE JOSEPH FOURRIER, Grenoble Cedex (FR)

( * ) Notice: Subject to any disclaimer, the term of this patent is extended or adjusted under 35 U.S.C. 154(b) by 0 days.

(21) Appl. No.: 14/456,178

(22) Filed: Aug. 11, 2014

(65) Prior Publication Data

US 2014/0350421 A1  Nov. 27, 2014

Related U.S. Application Data

(62) Division of application No. 12/624,175, filed on Nov. 23, 2009, now Pat. No. 8,805,485.

(60) Provisional application No. 61/116,870, filed on Nov. 21, 2008.

(51) Int. Cl.
*A61B 5/0444* (2006.01)
*A61B 5/04* (2006.01)
*A61B 5/00* (2006.01)

(52) U.S. Cl.
CPC ........... *A61B 5/0444* (2013.01); *A61B 5/04011* (2013.01); *A61B 5/4362* (2013.01); *A61B 5/7203* (2013.01); *A61B 5/725* (2013.01); *A61B 5/7246* (2013.01); *A61B 5/04012* (2013.01)

(58) Field of Classification Search
None
See application file for complete search history.

(56) References Cited

U.S. PATENT DOCUMENTS 4,945,917 A     8/1990  Akselrod et al.
5,372,139 A    12/1994  Holls et al.

(Continued)

OTHER PUBLICATIONS

Blumensath, Thomas, et al. "Blind Separation of Maternal and Fetal ECG's Using any Number of Channels" (2007) 7 pages.

(Continued)

*Primary Examiner* — Kennedy Schaetzle
(74) *Attorney, Agent, or Firm* — Occhiuti & Rohlicek LLP

(57) ABSTRACT

A method for processing cardiac signals includes accepting, from a sensor system, a set of one or more signals, the signals including components of a desired cardiac signal and components of a substantially periodic interfering signal. The method is applicable for extraction of desired fetal cardiac signals from signals with interference from the maternal cardiac signal. A periodicity of the interfering signal is determined, and one or more iterations of mitigating an effect of a component of the signals that exhibit periodicity at the determined periodicity of the interfering signal are performed. In some examples, the method further includes determining a periodicity of the desired cardiac signal, and performing one or more iterations of enhancing an effect of a component of the signals that exhibit periodicity at the determined periodicity of the desired cardiac signal.

5 Claims, 15 Drawing Sheets

(56) References Cited

U.S. PATENT DOCUMENTS

| | | | |
|---|---|---|---|
| 5,666,959 | A | 9/1997 | Deans et al. |
| 5,704,365 | A | 1/1998 | Albrecht et al. |
| 6,751,498 | B1* | 6/2004 | Greenberg et al. ............ 600/511 |
| 7,333,850 | B2 | 2/2008 | Marossero et al. |
| 2002/0193670 | A1* | 12/2002 | Garfield et al. ............... 600/304 |
| 2005/0288600 | A1* | 12/2005 | Zhang et al. .................. 600/510 |
| 2006/0253044 | A1* | 11/2006 | Zhang et al. .................. 600/512 |
| 2007/0066908 | A1 | 3/2007 | Graupe et al. |
| 2007/0260151 | A1 | 11/2007 | Clifford |
| 2008/0125668 | A1 | 5/2008 | Graupe et al. |

OTHER PUBLICATIONS

Sameni, Reza et al. "Multichannel ECG and Noise Modeling: Application to Maternal and Fetal ECG Signals" *EURASIP Journal on Advances in Signal Processing.* (vol. 2007) 14 pages.

Sameni, Reza, et al. "Model-Based Bayesian Filtering of Cardiac Contaminants from Biomedical Recordings" *Physiological Measurement.* vol. 29 (2008) pp. 595-613; DOI: 1031088/0967-3334/29/5/006.

Sameni, Reza, et al. "Multichannel Electrocardiogram Decomposition Using Periodic Component Analysis" *IEEE Transactions on Biomedical Engineering.* vol. 55 No. 8 (Aug. 2008) pp. 1935-1940.

Sameni, Reza, et al. "Noninvasive Extraction of Fetal Cardiac Signals from Maternal Abdominal Recordings." (Sep. 14, 2008) pp. 1-20.

Sameni, Reza, et al. "Thesis: Extraction of Fetal Cardiac Signals from an Array of Maternal Abdominal Recordings" Institut Polytechnique de Grenoble & Sharif University of Technology (Jul. 2008) 109 pages.

Semeni, Reza "Extraction of Fetal Cardiac Signals from an Array of Maternal Abdominal Recordings" Presentation at Grenoble INP, Grenoble, France (Jul. 7, 2008) 40 pages.

Syed, Zeeshan, et al. "Clustering and Symbolic Analysis of Cardiovascular Signals: Discovery and Visualization of Medically Relevant Patterns in Long-Term Data Using Limited Prior Knowledge" *EURASIP Journal on Advances in Signal Processing.* (vol. 2007) 16 pages.

\* cited by examiner

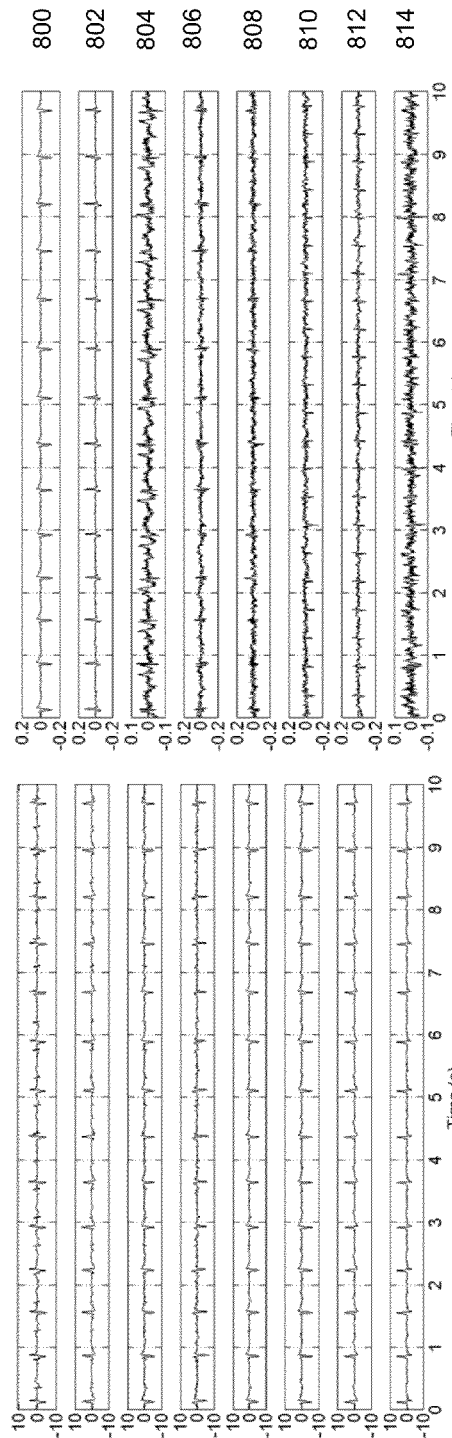
Fig. 8A
Fig. 8B
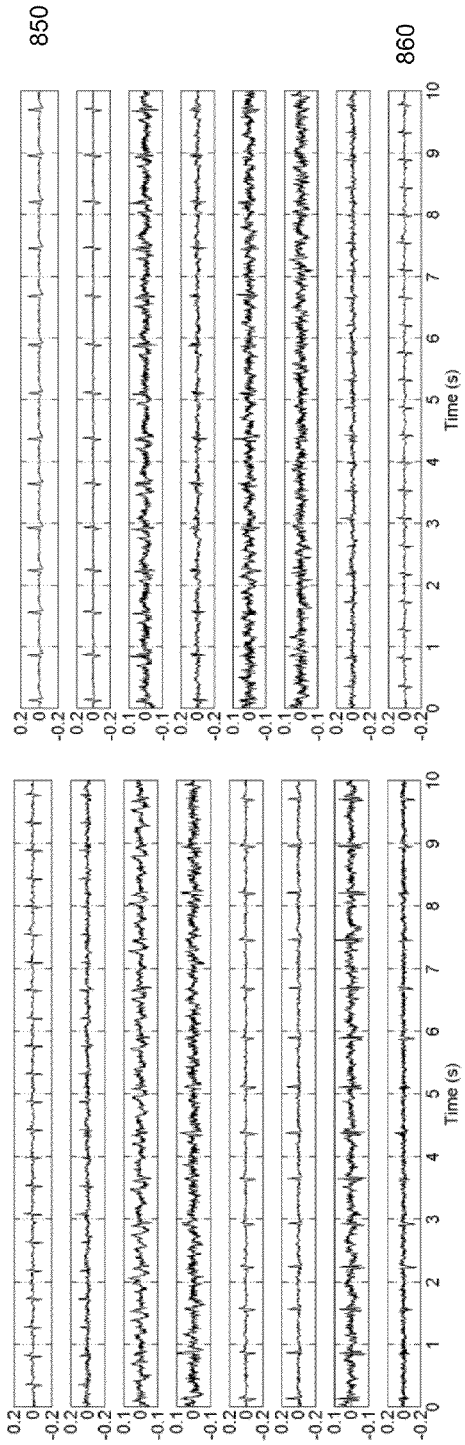
Fig. 8C
Fig. 8D

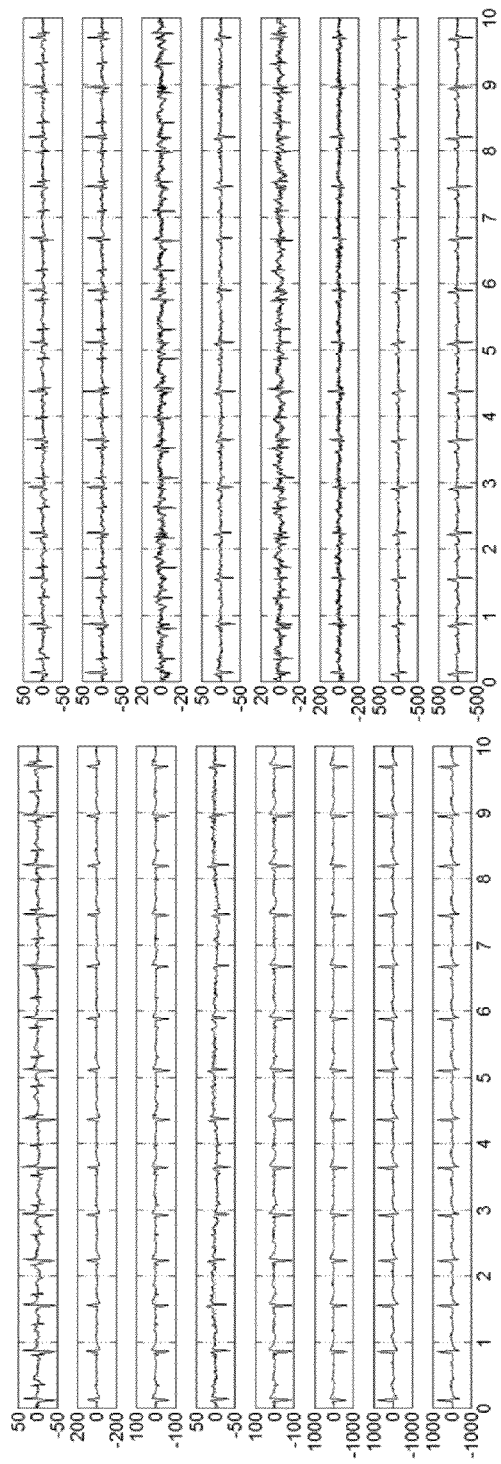
Fig. 9A
Fig. 9B
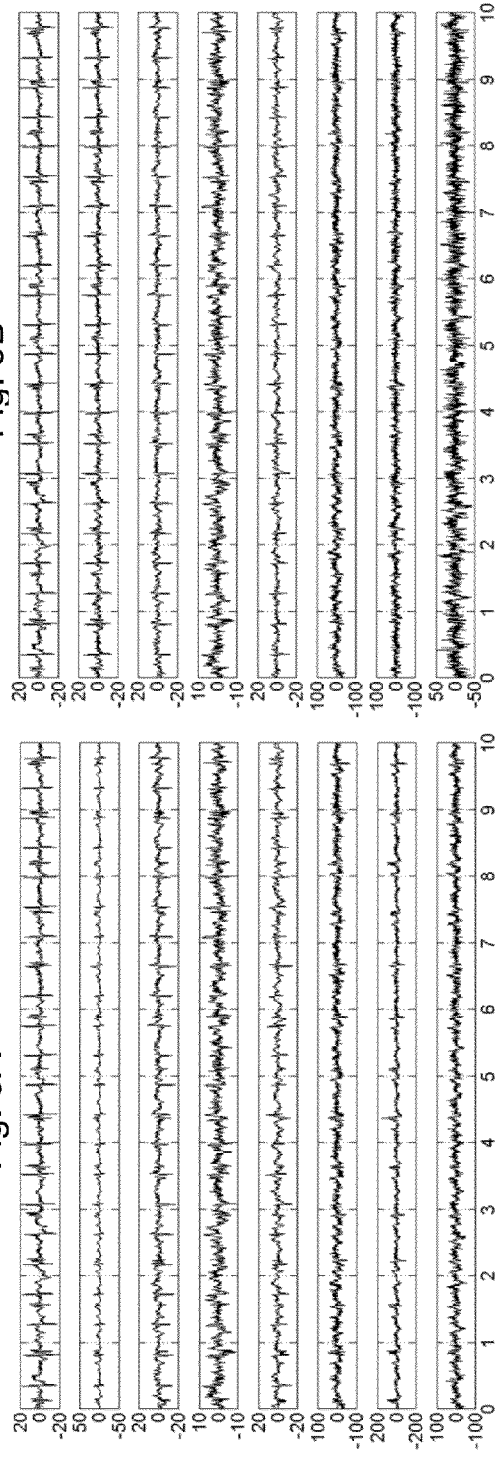
Fig. 9C
Fig. 9D

EXTRACTION OF FETAL CARDIAC SIGNALS

CROSS-REFERENCE TO RELATED APPLICATIONS

This application is a divisional of U.S. application Ser. No. 12/624,175, filed Nov. 23, 2009, now U.S. Pat. No. 8,805,485, which claims priority to U.S. Provisional Application Ser. No. 61/116,870, filed Nov. 21, 2008, the contents of which are incorporated herein by reference.

BACKGROUND

This invention relates to extraction of fetal cardiac signals from signals acquired from a subject.

Monitoring of fetal cardiac signals can be difficult due to the presence of both maternal and fetal cardiac signals in raw signals acquired from a subject, as well as a relatively low fetal signal level relative to the maternal signal and other noise sources. One approach to acquiring fetal cardiac signals involves the use of electrodes, such as surface electrodes positioned on the maternal abdomen, which may provide lower signal to noise levels as compared to invasive approaches to acquiring fetal signals (such as using fetal scalp electrodes).

SUMMARY

In a general aspect, a method for processing signals includes accepting, from a sensor system, a set of one or more signals. The signals include components of a desired signal and components of a interfering signal having a periodicity. The method further includes determining, by a processing engine, the periodicity of the interfering signal; and performing, by the processing engine, one or more iterations of mitigating an effect of a component of the signals that exhibits periodicity at the determined periodicity of the interfering signal to form a processed signal.

Embodiments may include one or more of the following. The method includes providing the processed signal to a display system.

The interfering signal includes at least one of a substantially periodic and a pseudo periodic signal. Determining the periodicity of the interfering signal includes determining a time varying period of said signal. The method includes determining a periodicity of the desired signal and performing one or more iterations of enhancing an effect of a component of the signals that exhibits periodicity at the determined periodicity of the desired signal.

The desired signal is a cardiac signal. The interfering signal includes a second cardiac signal. The periodicity of the interfering signal comprises a quantity characterizing a heartbeat period of the second cardiac signal. The quantity characterizing the heartbeat period of the second cardiac signal comprises an estimated R-R interval. The desired cardiac signal comprises a fetal cardiac signal and the interfering signal comprises a maternal cardiac signal. The desired cardiac signal comprises a cardiac signal of a first fetus and the interfering signal comprises a cardiac signal of a second fetus. The interfering signal further includes a maternal cardiac signal.

Mitigating the effect of a component of the signals that exhibit periodicity at the determined periodicity of the interfering signal includes identifying a relative contribution of the component of the signals that exhibit periodicity at the determined periodicity; and processing the signals according to the identified relative contribution. Identifying the relative contribution of the component of the signals that exhibit periodicity at the determined periodicity includes computing a generalized eigenvalue based on correlation of the signals at the determined periodicity of the interfering signal. Processing the signals according to the identified relative contribution includes applying a Bayesian filtering approach.

In another general aspect, a cardiac monitoring system includes an input subsystem for accepting signals. The signals include components of a desired signal and components of an interfering signal having a periodicity. The cardiac monitoring system further includes a data processing system for processing the accepted signals. The data processing system is configured to perform the steps of determining the periodicity of the interfering signal, and performing one or more iterations of mitigating an effect of a component of the signals that exhibits periodicity at the determined periodicity of the interfering signal. The cardiac monitoring system also includes a data output subsystem for providing information determined from the processed signals.

Embodiments may include one or more of the following. The desired signal is a cardiac signal.

In a further general aspect, software embodied on a computer-readable medium includes instructions for causing a data processing system to accept a set of one or more signals, the signals including components of a desired signal and components of a interfering signal having a periodicity; determine the periodicity of the interfering signal; and perform one or more iterations of mitigating an effect of a component of the signals that exhibits periodicity at the determined periodicity of the interfering signal.

In another general aspect, a method for processing a input signal that includes a pseudo-periodic signal present with another signal includes accepting the input signal. The input signal is representable as a vector signal in a multidimensional vector space. The method further includes forming a phase signal representing a time-varying periodicity of the pseudo-periodic signal; identifying a subspace of the vector space that exhibits correlation at the time-varying periodicity; forming a component of the input signal according to the identified subspace; and processing the input signal to either enhance or to mitigate and effect of the formed component to produce a processed signal.

Embodiments may include one or more of the following. Accepting the input signal includes accepting a biosignal. The pseudo-periodic signal has a periodicity related a periodic biological process. The biosignal includes a signal acquired by sensing a signal from a human body, and the periodic biological process includes a cardiac process.

The method further includes presenting the processed signal on a display. Forming the phase representation includes identifying repetitions of a signal characteristic in the input signal. Identifying the subspace includes determining a generalized eigenspace from a correlation of the input signal at a time varying lag determined from the phase representation and from a correlation of the input signal at zero lag. Forming the component of the input signal according to the identified subspace includes projecting the input signal onto the eigenspace. Processing the input signal to either enhance or to mitigate an effect of the formed component to produce a processed signal includes at least one of adding or subtracting the projection of the signal onto the eigenspace.

The method for extraction of fetal cardiac signals described herein has a number of advantages. In general, the method enhances a weak fetal signal that is overshadowed by strong maternal electrocardiogram (ECG) or respiration interference. The retrieved fetal signal preserves clinical information such as signal morphology and the multi-dimensionality of the signal. For instance, the multi-dimensional nature of the source (e.g., the fetal heart) is preserved, facilitating diagnosis along more than one axis and allowing determination of the angle of the fetal cardiac dipole and the presentation or movement of the fetus along the fetal body axis. A multi-dimensional dipole reconstruction also allows a Dower-like transform to be performed to reconstruct the surface map of the mother's abdomen and to assess metrics such as QT dispersion. Referring to FIG. 13, standard clinical metrics of an ECG 350, such as QT interval 352 and ST elevation 354, can also be evaluated using the extracted fetal signals. Furthermore, localization of the R-peak 356 of a fetal ECG allows for accurate evaluation of heart rate variability (HRV) metrics.

Cardiac signals can be analyzed online in real time or offline after a measurement. Real-time fetal ECG analysis provides the opportunity to observe the fetal response to inter-uterine contractions and to identify abnormalities in the fetal ECG (e.g., arrhythmias and QT lengthening) associated with such stress.

The measurement and analysis can be used at any time during pregnancy, and does not depend on fetal presentation or gestational age. The method can be used prior to or during labor. Multiple fetuses can be monitored simultaneously and separated for individual diagnosis. The analysis is robust against movement of the fetus or the electrodes. The measurements are noninvasive, thus posing little or no risk to the mother or the fetus. Simple monitoring equipment can be used, allowing for inexpensive and relatively quick measurements.

The analysis is applicable to degenerate mixtures of maternal and fetal cardiac signals and noise without any prior assumptions about the dimensionality of the maternal or fetal cardiac signal subspaces. Mixtures of signals having fewer numbers of channels than expected sources can be evaluated without losing the important clinical fetal cardiac components during denoising. Maternal interference and other noise can be eliminated by using even a small number of recording channels and without reducing the rank of the observations during the denoising procedure. At most, a single reference channel (e.g., a maternal reference channel) is used, but the reference channel may be recorded from any arbitrary channel and is not constrained to be morphologically similar to the contaminating waveform.

BRIEF DESCRIPTION OF THE DRAWINGS

FIG. 8A is a graph of an ECG dataset.

FIG. 8B is a graph of maternal ECG components extracted from the dataset of FIG. 8A.

FIG. 8C is a graph of fetal ECG components extracted from the dataset of FIG. 8A.

FIG. 8D is a graph of maternal and fetal ECG components extracted from the dataset of FIG. 8A.

FIG. 9A is a graph of an ECG dataset.

FIGS. 9B-9F are graphs showing the results of 1-5 iterations, respectively, of removal of the maternal subspace from the dataset of FIG. 9A

DETAILED DESCRIPTION

Noninvasive monitoring of fetal cardiac signals is often made difficult by noise and interference from the stronger maternal cardiac signal. In order to analyze the fetal cardiac signal, signals recorded from the body surface of a pregnant woman are processed to obtain a purified fetal cardiac signal. Maternal cardiac artifacts, which are the dominant source of interference in fetal signals, are removed from noisy signal mixtures. After the maternal cardiac interference is removed, depending on the signal quality and fetal gestational age, the quality of the fetal cardiac signal can be further improved in a post-processing step. Signal quality of the ECG electrode recordings can be assessed by comparing temporal and spectral coherence between recorded channels.

The extracted fetal signal is multidimensional (i.e., it represents more than a single quantity, such as heart rate, or a single ECG channel) and contains diagnostic cardiac information pertaining to the health of the fetus or fetuses carried by the mother. For instance, the presentation of the fetus can be determined from the multidimensional fetal cardiac signal. Standard clinical metrics related to the morphology of the fetal cardiac signal are also accessible.

The term "cardiac signal" as used herein refers to any waveform containing morphological characteristics of a cardiac signal, such as an electrocardiogram (ECG) or magnetocardiogram (MCG). In some cases, the techniques described herein are described with reference to the ECG; however, these techniques apply equally to the MCG or any similar modalities of cardiac monitoring.

1 DATA COLLECTION

From a signal processing perspective, the heart can be considered as a distributed signal source with infinite dimensions. Depending on the distance between the heart (either the maternal heart or the fetal heart) and electrodes positioned on the body surface, the electrical or electromagnetic activity of the heart can be approximated as a distributed source with a lower rank subspace. The study of the components of such subspaces provides valuable clinical information about the vectorcardiograph (VCG) representation of the cardiac waveforms and the well-being of the heart. To obtain a VCG representation of cardiac waveforms of an adult, signals are recorded from different positions on the body, with each signal containing specific information about the cardiac activity represented in unique morphology (shape) and frequency content. However, since the fetus is not directly accessible from more than one angle (and even then only during labor), fetal VCG representation is only achievable by signal processing techniques.

Figure 1:
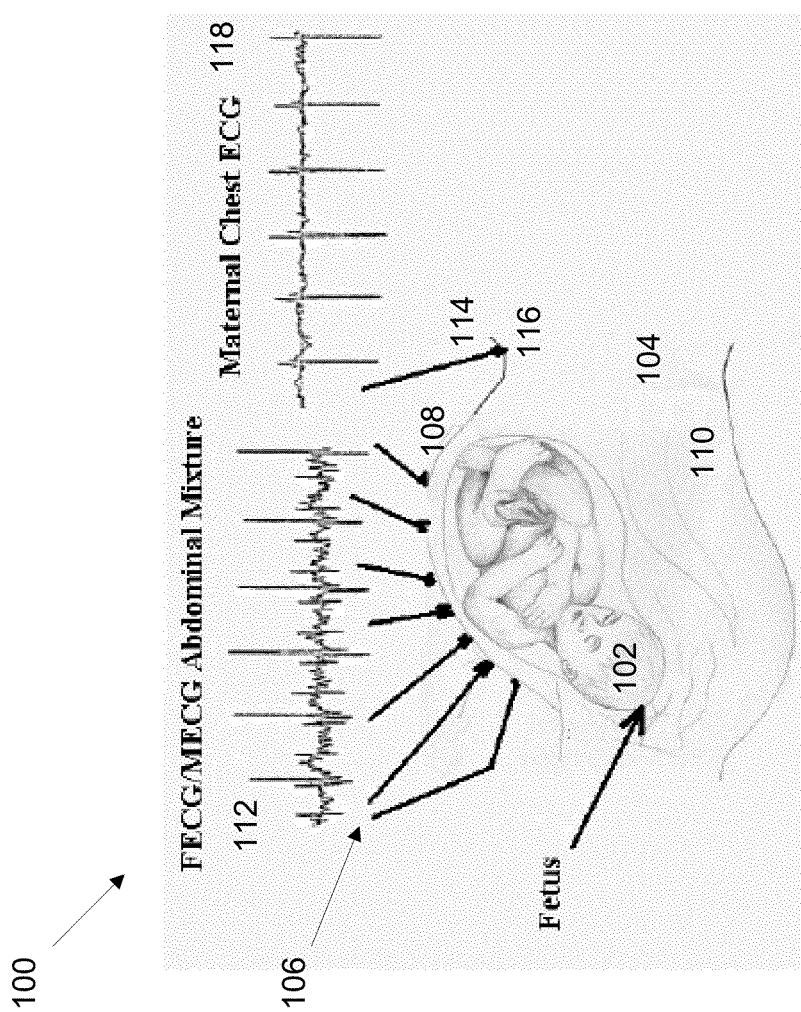
FIG. 1 is an illustration of the collection of fetal abdominal electrocardiogram (ECG) from multiple electrodes.

Referring to FIG. 1, a noninvasive system 100 for fetal cardiac signal extraction makes use of signals representative of an ECG of a fetus 102 and an ECG of a pregnant woman 104. The signals are acquired from a set of signal electrodes 106 distributed over the maternal abdomen 108 and/or lower back 110 and thus far from the maternal heart. A representative signal 112 acquired by one of the signal electrodes 106 shows that the signal is dominated by maternal ECG, although fetal ECG is also present. In some examples, the fetal heartrate may be determined using other sensing modes such as ultrasound or the use of a fetal scalp electrode. However, the full representation of the ECG is more informative than these techniques.

In some embodiments, only one maternal abdominal sensor is used. However, for more detailed studies, the use of multiple sensors well-distributed over the maternal body reduces the risk of degenerate mixtures of signals and improves the quality of the fetal signal extraction. This is because a more accurate representation of the maternal ECG allows it to be removed more effectively from the mixture. For instance, between six and sixteen signal electrodes 106 may be used to retrieve the fetal waveform morphology, although fewer electrodes can be used when the fetal ECG is strong. Even more electrodes may be used for dynamic reselection of channels containing a stronger fetal signal contribution, especially during long monitoring sessions when the fetus may move.

The acquired signals also include one or more reference signals that provide information about the maternal heart. These signals may include signals from a maternal reference channel associated with a set of one or more maternal reference electrodes 114 placed on the woman's chest 116 near the heart from which a reference maternal cardiac signal 118 can be determined. Alternatively, maternal cardiac electrodes may be placed on the navel, hand, or leg of the pregnant woman. In some embodiments, a reference signal is obtained from a signal acquired by one of the signal electrodes 106 and which has a dominant maternal heartbeat. In other examples, other sensing modes are used to determine the maternal heartrate, for example, using one or more of ultrasound, imaging, bloodpressure sensing. The maternal reference channel provides information regarding the maternal heartrate, for example, based on maternal fiducial point or beat (R-peak) detection. The morphology of the maternal reference channel is not constrained to match that of the contaminating maternal signal recorded by the abdominal signal electrodes 106.

In general, the data processing methods described below are not sensitive to the sampling rate of the maternal and fetal ECG, provided the waveforms are not disturbed. However, data sampling at 500 Hz-1000 Hz, quantized with 14-16 bits, generally enables a high quality fetal ECG signal to be obtained. Higher sampling rates may also be used but require a higher processing load.

2 DATA PROCESSING

The acquired signals are treated as a vector, time-sampled, zero-mean signal x(t). That is, if there are N electrodes, the signal is represented as an N-dimensional vector. The vector signal is modeled as having three components:

$$x(t)=x_f(t)+x_m(t)+x_n(t),$$

where $x_f(t)$ is a desired N-dimensional component of the signal representing the fetal cardiac signal (without any reduction in dimensionality from the originally acquired signals), $x_m(t)$ is the maternal interference component, and $x_n(t)$ is the noise component. Although represented as N-dimensional signals, some or all of the signal or noise components are not necessarily full rank (i.e., their variation may be confined to a lower-dimensional subspace).

The maternal and fetal signals, $x_m(t)$ and $x_f(t)$, respectively, are each characterized by a pseudo-periodic structure that is repeated in all the channels synchronous with the maternal and fetal heart beats, respectively. The difference in the rates of the maternal and fetal signals enables a separation of the signals as described further below.

In general, the methods described herein identify and remove any periodic structure in the acquired signals that is synchronous with the reference maternal ECG R-peaks. That is, the maternal signal is removed by determining the maternal heartrate and removing components of the recorded signal that exhibit periodicity at that heartrate. Because the fetal heartbeat is generally non-synchronous with the maternal heartbeat, the fetal signal can be preserved and enhanced.

2.1 Baseline Wander Removal

Figure 2:
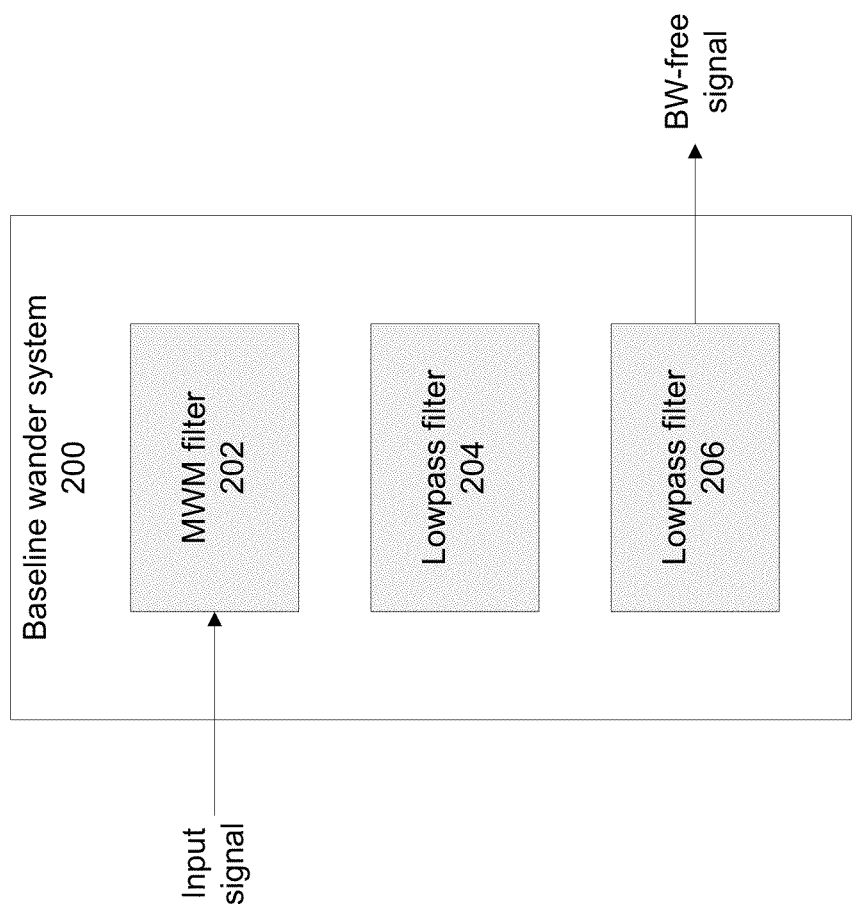
FIG. 2 is a block diagram of a baseline wander removal system.
Figure 3:
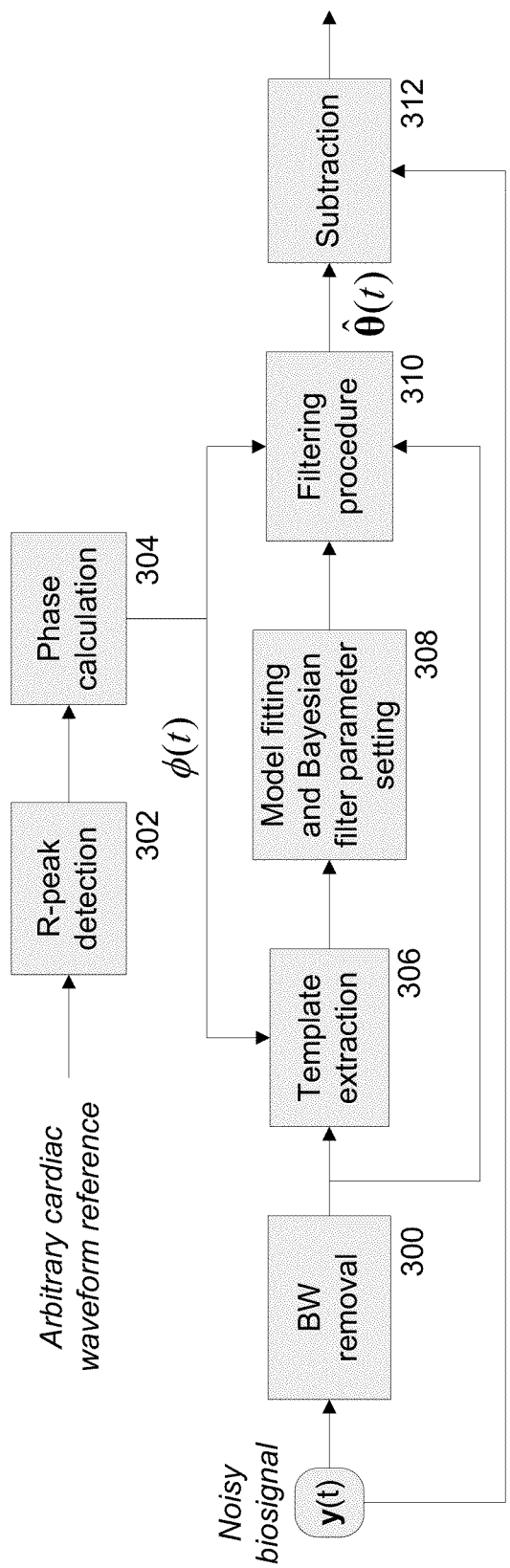
FIG. 3 is a flow chart of a filtering scheme.

Referring to FIGS. 2 and 3, in some embodiments, after acquisition of the raw electrode signals, baseline wander (BW) of the data is removed by a baseline wander system 200 (step 300) before further processing of the signals. In some examples, a two-stage moving window median (MWM) filter 202 with variable window lengths (for instance, set by default to 200 ms and 600 ms, respectively) is used, followed by a lowpass filter 204 with a variable cutoff frequency (for instance, set by default to 5 Hz). The estimated BW obtained from filters 202 and 204 is subtracted from the input signal to achieve a BW-free signal. An additional lowpass filter 206 with a variable cutoff frequency (for instance, set by default to 200 Hz) may also be used to suppress out-of-band noise. Alternatively, another effective BW removal strategy may be employed.

2.2 Cardiac Phase Signal

Figure 13:
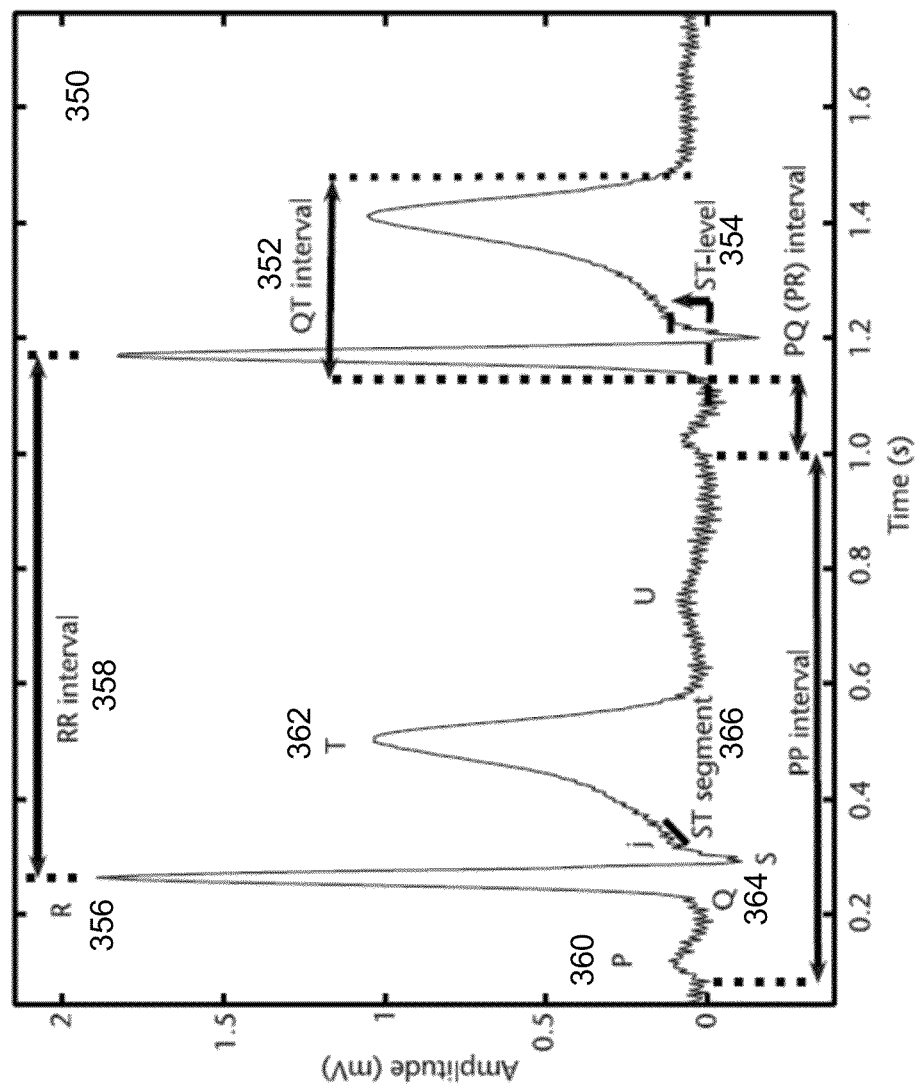
FIG. 13 is a graph of an exemplary ECG.

Cardiac waveforms have a pseudo-periodic structure that is repeated for each cycle of the heartbeat but with normal RR-period deviations of up to 20% over the preceding RR interval (i.e., RR interval 358 in FIG. 13). Referring to FIG. 4A, to represent this pseudo-periodicity for the cardiac source(s) of interest (i.e., the mother or the fetus), a cardiac phase signal φ(t) is defined for a reference cardiac signal 400 received from an arbitrary reference channel (e.g., the maternal reference channel). φ(t) sweeps over [−π, π] for each cardiac cycle of reference signal 400. Under this definition of φ(t), samples of data having similar phase values represent corresponding stages in the depolarization/repolarization cycle of the heart and are morphologically similar.

Referring to FIGS. 3 and 4A, to define φ(t), R-peaks 404 of the reference cardiac waveform 400 are detected (step 302) using peak detectors, matched filters, or another method capable of detecting R-peaks. Alternatively, R-peaks 404 may be detected using a time sample in which the cardiac beat has maximal 'similarity' with a given reference beat. Based on R-peaks 404, φ(t) is defined (step 304) as a saw-tooth signal 402 that linearly sweeps over [−π, π] in each R-R interval, with each R-peak 404 fixed at φ(t)=0. Alternatively, non-linear mapping using, for instance, tanh functions may be used to construct φ(t).

Based on φ(t), a time-varying cardiac period $\tau_t$ 406 is defined as follows:

$$\tau_t = \min\{\tau | \phi(t+\tau) = \phi(t), \tau > 0\}.$$

That is, the signal samples at time t and at time $t+\tau_t$ have the same phase value and are morphologically similar. $\tau_t$ is updated on a beat-to-beat basis. In general, the cardiac phase signal $\phi(t)$ and the cardiac period $\tau_t$ may be defined for either the mother or the fetus, using the corresponding R-peaks.

The phase signal $\phi(t)$ provides a means for phase-wrapping the RR-interval onto a $[-\pi,\pi]$ interval. That is, an ECG, regardless of its RR-interval deviations, can be converted to a polar representation in which the ECG components in different beats (e.g., the P, Q, R, S, and T-waves) are roughly phase-aligned with each other, particularly over the QRS segment of the ECG. For instance, referring to FIG. 4B, a noisy cardiac signal 450 is depicted in a polar representation of the ECG using the phase $\phi(t)$ of the signal.

2.3 Signal Extraction from a Scalar Input Signal

To demonstrate the general technique, one can consider a scalar case in which N=1. That is, there is a single abdominal electrode signal, and the maternal heartrate is fixed with a period $\tau_t$. If the signal has a variance $\sigma_x^2$ a fixed autocorrelation at lag $\tau$ represented as $R(\tau)=E(x(t)x(t+\tau))/\sigma_x^2$, then a denoising function can be applied to the signal, for example based on the autocorrelation at lag $\tau$. An example of a denoising function is a Weiner filter. Generally, for a greater autocorrelation value, more of the signal is removed as representing a component that has periodicity that matches the maternal heartbeat.

In general, the maternal signal is not exactly periodic, and therefore analysis at a fixed lag may not be as effective as accounting for the variation periodicity. That is, the period $\tau_t$ may vary as a function of t. In this case, rather than an autocorrelation at a fixed lag, a time average at the time varying lag is used. For example, in the scalar case, the non-stationary covariance $\tilde{C}_x$, given as $$\tilde{C}_x = E_t(x(t+\tau_t)x(t)),$$

is computed from the data, where $E_t(\bullet)$ is an average over time (e.g., over a time window) that provides an approximation of the autocorrelation function. The time varying period may be determined, for example, by tracking the R-R interval in the maternal reference signal.

2.4 Signal Extraction from a Multidimensional Input Signal

In embodiments with multidimensional data (N>1) the scalar approach described above is modified to include an additional feature of identifying a linear subspace that exhibits a relatively high degree of synchronization with the maternal heartbeat.

Specifically, rather than determining the sample variance of a scalar signal, an N by N zero-lag stationary covariance matrix of the signals is computed as:

$$C_x = E_t\{x(t)x(t)^T\},$$

where $E_t\{\bullet\}$ represents an average over time (or expected value for a stochastic formulation). Using the definition of the time-varying cardiac period, the non-stationary covariance matrix at lag $\tau_t$ is computed as $$\tilde{C}_x = E_t\{x(t+\tau_t)x(t)^T\},$$

which contains measures of the periodicity of the random process x(t) with respect to the heartbeat. That is, all of the temporal information of the ECG is contained in e'. Furthermore, in some embodiments, $\tilde{C}_x$ can be guaranteed to be positive definite (i.e., symmetric and with real eigenvalues) by applying $$\tilde{C}_x \leftarrow (\tilde{C}_x + \tilde{C}_x^T)/2.$$

Figure 4B:
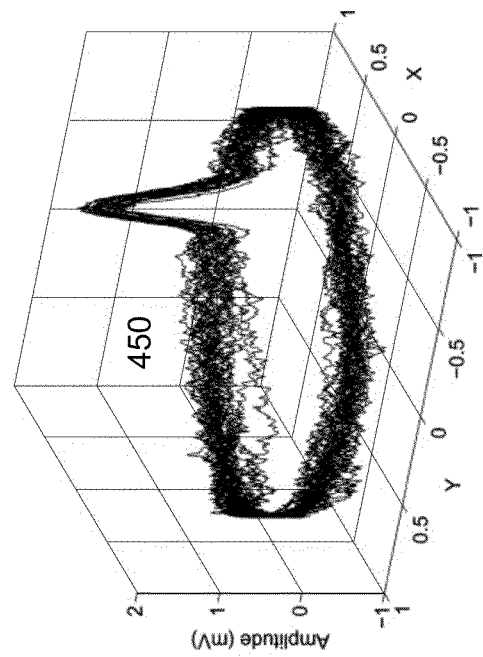
FIG. 4B is a polar representation of an exemplary ECG using the ECG phase signal.
Figure 4A:
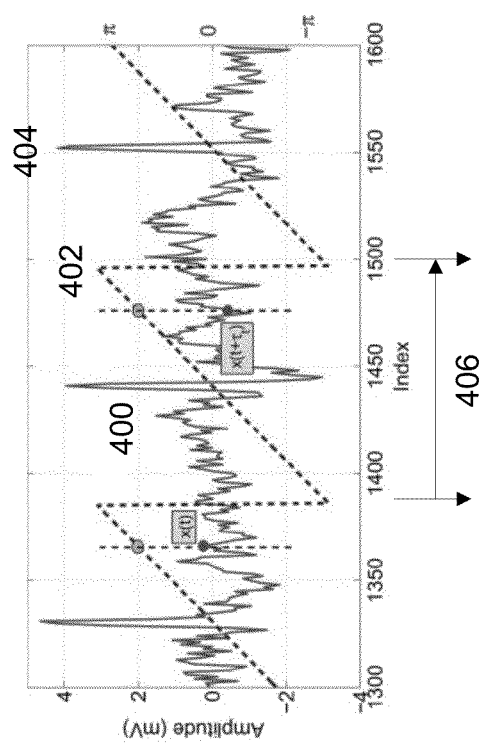
FIG. 4A is a graph of an exemplary cardiac signal and cardiac phase signal.

Considering the polar representations of each of the channels of x(t) (e.g., as shown in FIG. 4B), the matrix $\tilde{C}_x$ represents the covariance of the polar representation around its mean value. That is, $\tilde{C}_x$ contains a measure of the ECG periodicity extracted from the ECG R-peak information.

In general, the cardiac phase signal $\phi(t)$, the cardiac period $\tau_t$, and the matrix $\tilde{C}_x$ may be defined for either the mother or the fetus, using the corresponding R-peaks.

In some embodiments, as described in greater detail below, the acquired signals are processed using an iterative deflation method for fetal ECG denoising. The iterative method combines Pseudo-Periodic Component Analysis (PiCA) and a Kalman denoising scheme for removing the maternal ECG and enhancing the fetal ECG.

In some embodiments, as described in greater detail below, a general deflation method for subspace extraction is used to extract and enhance the fetal ECG. The method uses an appropriate linear transform (such as, but not limited to, PiCA), with a linear or nonlinear denoising scheme (such as, Kalman filters, Wavelet decomposition, or etc.) for separating any two intersecting subspaces of signal and noise.

2.4.1 Pseudo-Periodic Component Analysis (PiCA)

In some embodiments, a linear transformation based on generalized eigenvalue decomposition (GEVD) of covariance and lagged-covariance matrices using time-varying lags is computed. The transformation generates linear combinations of the input data array, ranked in order of resemblance with the periodicity of interest.

For instance, a linear subspace that exhibits relatively high synchronization with the maternal heartbeat is identified based on the computed covariance and autocorrelation matrices. In some examples, a one-dimensional subspace is identified based on a generalized eigenvector of the pair of matrices $(C_x, \tilde{C}_x)$ corresponding to the largest eigenvalue. Very generally, within the one-dimensional eigenspace, the scalar approach outlined above can be applied to reduce the contribution of the maternal periodic component according to the variance and autocorrelation values in that eigendirection.

More specifically, by GEVD of the matrix pair $(C_x, \tilde{C}_x)$, the matrices B and A are found such that $$B^T \tilde{C}_x B = \Lambda \text{ and } B^T C_x B = I,$$

where $\Lambda$ is the diagonal generalized eigenvalue matrix corresponding to the generalized eigenmatrix B, with real eigenvalues sorted in descending order along its diagonal. B, a transformation that simultaneously diagonalizes $C_x$ and $\tilde{C}_x$, is referred to as the periodicity ranking transform (PRT). The first eigenvector $b_1$, which corresponds to the largest generalized eigenvalue, maximizes the Rayleigh quotient:

$$J(b) = \frac{b^T \tilde{C}_x b}{b^T C_x b},$$

which, following the definitions of $C_x$ and $\tilde{C}_x$, is a measure of signal periodicity.

The transformed signals are then ranked in order of periodicity (i.e., in order of relevance to the cardiac signal of interest). The ranked transformed signals are represented as y(t), where $$y(t) = B^T x(t).$$

The components of y(t) (i.e., $y(t) = [y_1(t), \ldots, y_n(t)]^T$) are sorted according to their periodicity such that $y_1(t)$ is the most periodic component and $y_n(t)$ is the least periodic with respect to the R-peaks of the relevant ECG (step 306; also steps 500 and 550 in FIG. 5, discussed below).

For instance, for fetal ECG extraction, maternal and fetal ECG phases found from the maternal and fetal R-peaks may be defined as $\phi_m(t)$ and $\phi_f(t)$, respectively. The respective covariance matrices $\tilde{C}_x^m$ and $\tilde{C}_x^f$ can be found by averaging over the maternal and fetal periods. Then, the matrix $\tilde{C}_x$ used in the GEVD process may be set to any of the following matrices:

$$\tilde{C}_x = \tilde{C}_x^m$$

$$\tilde{C}_x = \tilde{C}_x^f$$

$$\tilde{C}_x = \tilde{C}_x^m - \tilde{C}_x^f.$$

If we assume the data to be prewhitened, the diagonalization of the above matrices is equivalent to finding, respectively, (1) the most periodic components with respect to the maternal ECG; (2) the most periodic components with respect to the fetal ECG; and (3) the most periodic components with respect to the maternal ECG while being the least periodic components with respect to the fetal ECG. In this latter case, the extracted components gradually change from the maternal ECG (the first components of y(t)) to the fetal ECG (the last components of y(t)). The latter two cases may be difficult to implement in practice, as the extracted fetal R-peaks must be known in order to form the $\tilde{C}_x^f$ matrix.

In other embodiments, PiCA may be used to analyze twin fetal ECG (or MCG). In this case, after preprocessing of the data, the maternal ECG (or MCG) is removed using PiCA. An independent component analysis is used to find coarse estimates of the fetal ECGs or MCGs). The maternal ECG (or MCG) is then reidentified using maternal/fetal PiCA as $$\tilde{C}_x = \tilde{C}_x^m - (\tilde{C}_x^{f1} + \tilde{C}_x^{f2}).$$

The fetal ECG (or MCG) is then determined in a post-processing step. PiCA is also extensible to use with multiple fetuses (e.g., triplets or higher order multiples).

2.4.2 Denoising

Referring again to FIG. 3, the ranked signals y(t) are subjected to adenoising procedure, such as a wavelet denoising process. For instance, a multichannel extension of a Bayesian filtering framework is used to denoise the first M ($1 \leq M \leq N$) components of y(t). For instance, a Kalman filter and Kalman smoother use a priori information from ECG dynamics and noisy observations to estimate the true ECG and, optionally, to remove maternal ECG contaminants. Other, less optimal, denoising methods may also be used.

In the simplest case of M=1, the filtering is implemented as a single channel denoising.

In this framework, the components of $y_i(t)$ (i=1 . . . M) are considered to be noisy observations of hidden states of a dynamic system. Each of the entries of the state vector is modeled with a summation of small waves, such as (but not limited to) Gaussian functions, which are pseudo-periodically repeated with the cardiac phase signal $\phi(t)$.

A state-space representation of the model is used for filtering; the parameters of the model are trained from the average and standard deviations of the polar representation of the noisy signal of FIG. 4B (step 308). For online implementation of the filtering, the most recent cardiac beats are used in training the model and the parameters are updated in real time.

Using this filtering framework, a denoised estimate $\hat{\theta}(t)$ of the cardiac signals is determined (step 310). If the maternal cardiac signals are of interest, the denoised cardiac signals are given as $z(t) = \hat{\theta}(t)$. If the residual non-maternal signals are of interest (e.g., for removal of the maternal ECG/MCG), the denoised signals are given as $z(t) = y(t) - \hat{\theta}(t)$ (step 312).

The denoised signal z(t) is then transformed back to the sensor space using the inverse PRT, producing a denoised version of x(t).

2.5 Iterative Subspace Removal

Subspace decomposition by deflation aims to decompose degenerate mixtures of signal and noise or artifacts without prior knowledge of the subspace dimensions and without reducing the dimensions of the data. That is, $$x(t) = x_{signal}(t) + x_{noise}(t)$$

and $$y(t) = B^T x(t) = B^T (x_{signal}(t) + x_{noise}(t)) = y_{signal}(t) + y_{noise}(t)$$

Subspace decomposition by deflation breaks the linearity by combining single-channel denoising and multi-channel decomposition under the assumptions that (1) the desired signals in different channels are dependent such that processing gain is achieved through multichannel analysis; and (2) some information is available about the desired signals such that the desired and undesired parts of the signals can be roughly separated using linear/nonlinear filters.

Figure 5A:
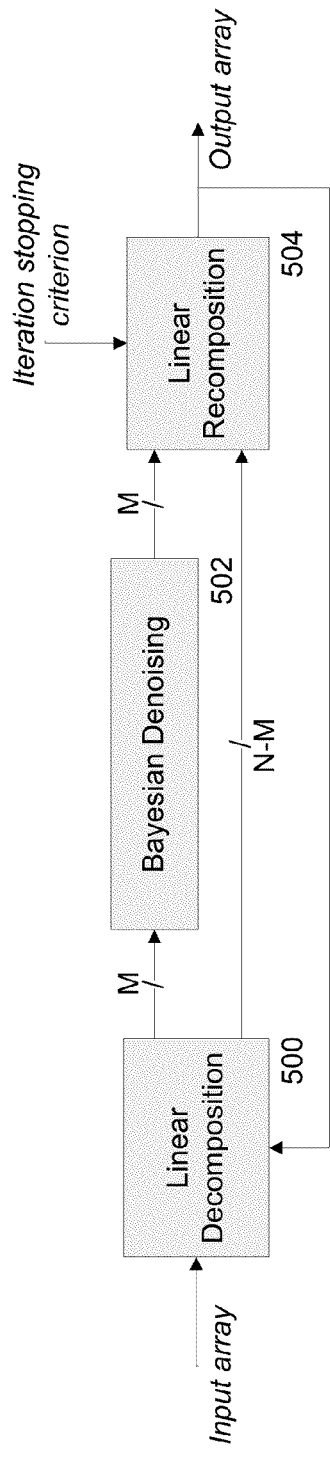
FIGS. 5A and 5B are block diagrams of an iterative subspace removal scheme.

Referring to FIG. 5A, the process of projection (i.e., linear decomposition of the input signals) using a periodicity ranking transform (step 500), denoising using the Bayesian framework (step 502), and back-projection (i.e., linear recomposition of the denoised signals) using the inverse PRT (step 504) are repeated in one or several iterations to gradually purify the observed signals. At each iteration, one eigendirection corresponding to the largest contribution of a contaminant signal (e.g., the maternal ECG) is identified and the effect of the contribution is reduced. This iteration may be performed a number of times, for example, a fixed number of iterations, or based on a degree of any remaining maternal contribution at the output of each iteration.

Figure 5B:
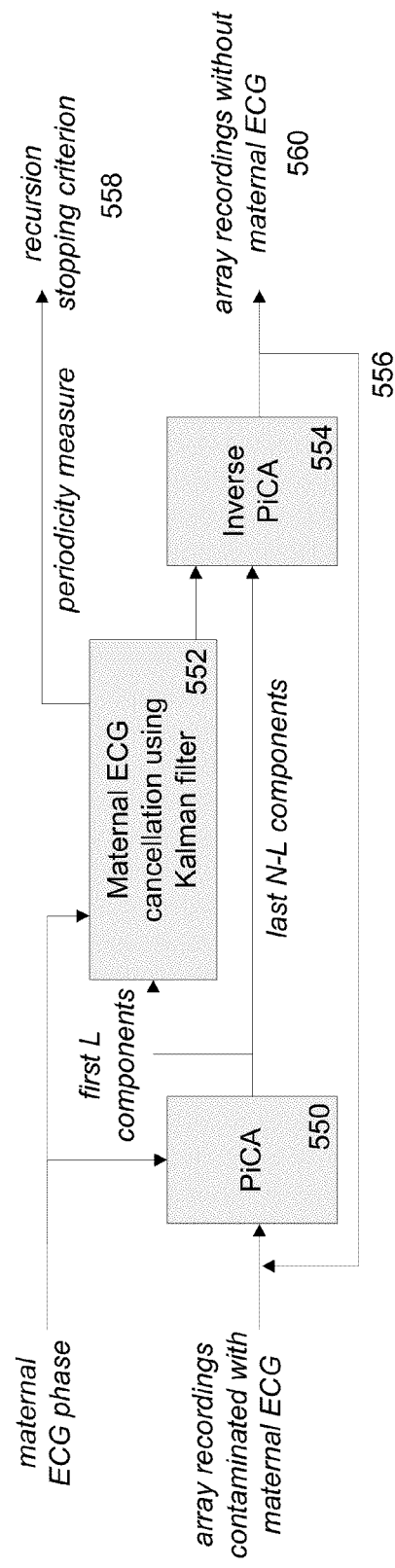

Referring to FIG. 5B, when applied to maternal ECG cancellation, an array of signal recordings contaminated with maternal ECG are input into a PiCA algorithm (550) along with the maternal ECG phase. The first L components output from the PiCA algorithm (i.e., the L components with periodicity closest to the desired periodicity) undergo maternal ECG cancellation using a Kalman filter (552). The L filtered components and the (N-L) remaining unfiltered components are recomposed by an inverse PiCA algorithm (554). This step effectively removes any scaling and ordering issues introduced by PiCA algorithms or other independent component analysis (ICA) algorithms. The retransformed data is iteratively processed (556) until a recursion stopping criterion (558) is achieved, at which point data without maternal ECG (560) is output.

Figure 6:
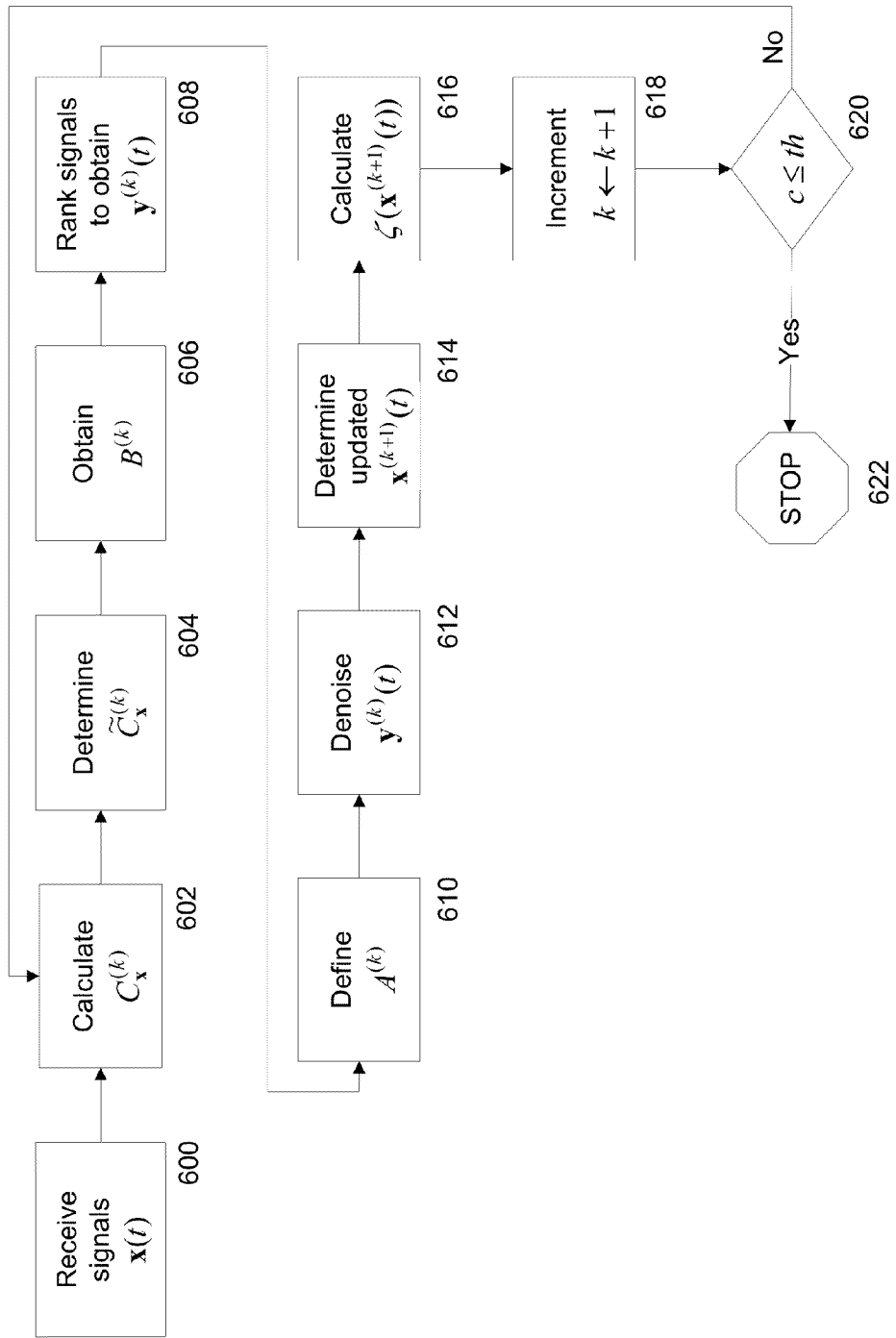
FIG. 6 is a flow chart of iterative subspace decomposition.

Referring to FIG. 6, the iterative subspace decomposition process is shown in more detail.

1. A set of input signals $x^{(k)}(t) = x(t)$ is received, where k is an iteration index and is set initially to 0 (step 600).
2. The matrix $C_x^{(k)}$, which is the covariance matrix of $x^{(k)}(t)$, is calculated (step 602).
3. The matrix $\tilde{C}_x^{(k)}$, which contains the desired statistics of $x^{(k)}(t)$, is then determined (step 604).
4. $B^{(k)}$, which is the transpose of the decomposition matrix found by generalized eigenvalue decomposition of the matrix pair $(C_x^{(k)}, \tilde{C}^{(k)})$ (i.e., $B^{(k)} \leftarrow GEVD(C_x^{(k)}, \tilde{C}_x^{(k)})^T$, is obtained (step 606).
5. The transformed signals are ranked in order of periodicity, giving $y^{(k)}(t) \leftarrow B^{(k)} x^{(k)}(t)$ (step 608).
6. The matrix $A^{(k)} = [a_1^{(k)}, \ldots, a_N^{(k)}] \leftarrow B^{(k)-1}$ is defined (step 610), where $a_j^{(k)}$ is the j-th column vector of $A^{(k)}$.
7. A denoising function $G(\cdot)$ is applied to the first M channels of $y^{(k)}(t)$ to remove the undesired components and to keep the desired components of each channel of $y^{(k)}(t)$ (step 612). The output of the denoising block in channel j is $s_j^{(k)}(t)$. The overall output of the denoising function is $s^{(k)}(t) = [s_1^{(k)}(t), \ldots, s_M^{(k)}(t)]^T \leftarrow G(y^{(k)}(t))$.

8. The updated signals $x^{(k+1)}(t)$ of the iteration are determined as $x^{(k+1)}(t) \leftarrow x^{(k)}(t) - \Sigma_{j=1}^{M} a_j^{(k)} s_j^{(k)}(t)$ (step 614).

9. $\zeta(x^{(k+1)}(t))$, which is a measure of the desired subspace removal used as a stopping criterion for the iterative subspace decomposition algorithm, is calculated (step 616): $c \leftarrow \zeta(x^{(k+1)}(t))$.

10. k is incremented: $k \leftarrow k+1$ (step 618).

11. c is compared to a predefined threshold value th (step 620). If $c \leq th$, the iterative subspace removal process is stopped (step 622). Otherwise, a further iteration is performed (step 624).

The output of each iteration of the subspace removal algorithm can be represented in compact form as $$x^{(k)}(t) = x(t) - \sum_{i=0}^{k-1} \sum_{j=1}^{M} a_j^{(i)} s_j^{(i)}(t).$$

The number of iterations performed depends on the dimensions of the removed subspace. In general, for cardiac signals, between three to six iterations are typically used. Thus, for practical implementations, the number of iterations may be fixed (e.g., at six iterations for cardiac applications). Alternatively, in each iteration the projected signal y(t) may used to determine whether to continue or stop the subspace removal algorithm. Since the components of y(t) are ranked according to their resemblance with the contaminating signal (e.g., the maternal ECG), each iteration removes the signals that are least important to the desired signal (e.g., the fetal ECG).

The following criterion may be used as an overall periodicity measure (PM) for $x^{(k)}(t)$ in each iteration:

$$\zeta(x^{(k)}(t)) = \frac{\text{trace}(\tilde{C}_x^{(k)})}{\text{trace}(C_x^{(k)})},$$

where $C_x^{(k)}$ and $\tilde{C}_x^{(k)}$ are the covariance matrices calculated for the signal $x^{(k)}(t)$. Under this definition, $0 \leq \zeta(x^{(k)}(t)) \leq 1$, and the iterative subspace removal algorithm is stopped when the PM falls below a small predefined threshold $0 \leq th \leq 1$ (for instance, by default set at th=0.05).

Although only two matrices ($C_x$ and $\tilde{C}_x$) are jointly diagonalized, the results are still robust to deviations of heartbeat and noise. The reason is that the time lags $\tau_t$ required in the calculation of $\tilde{C}_x$ are extracted from the beat-to-beat information of the ECG. This robustness may be further improved by splitting the information of the RR-interval that is carried by $\tilde{C}_x$ into several matrices that contain local information about the ECG cycle. Referring to the exemplary ECG cycle 350 shown in FIG. 13, these matrices contain information such as the morphology of P-waves 360 and T-waves 362, QRS complex 364, ST segment 366, QT interval 362, etc. These matrices can then be approximately diagonalized using joint approximate diagonalization methods.

The iterative subspace removal algorithm is also effective when signals are collected from a small number of electrodes. In other embodiments, when the number of observed channels is high and/or the desired components are strongly represented in the observed signals, one iteration of periodicity ranking transformation, denoising of the relevant channels, and back-projection of the desired components may be sufficient.

In some examples, a multidimensional subspace is identified at each iteration, for example, corresponding to a number of the largest generalized eigenvalues. The number of generalized eigenvalues may be fixed may be dependent on the data. The reduction in the maternal component is effected according to the eigenvalue associated with that direction. In some examples, the full N-dimensional space is used in each iteration.

2.6 Extraction of Desired Waveforms

Once the observed signals have been sufficiently purified as described above, the maternal cardiac interference is removed and the desired fetal signals are extracted. In this case, rather than identifying the maternal heartbeats, the fetal heartbeats are identified in the remaining signal. In this enhancement phase, in some examples, a subspace, which exhibits periodicity at the fetal heartrate, is enhanced. As in the attenuation of the maternal signal, one or more iterations may be performed, and at each iteration, one, a subset, or the full N-dimensional space may be processed. Note that in some examples, if the iterations of removal of the maternal signal are continued until the maternal signal no longer dominates the fetal signal, the fetal periodicity may become evident without enhancement even if it was not apparent in the original signal.

Figures 7A, 7B:
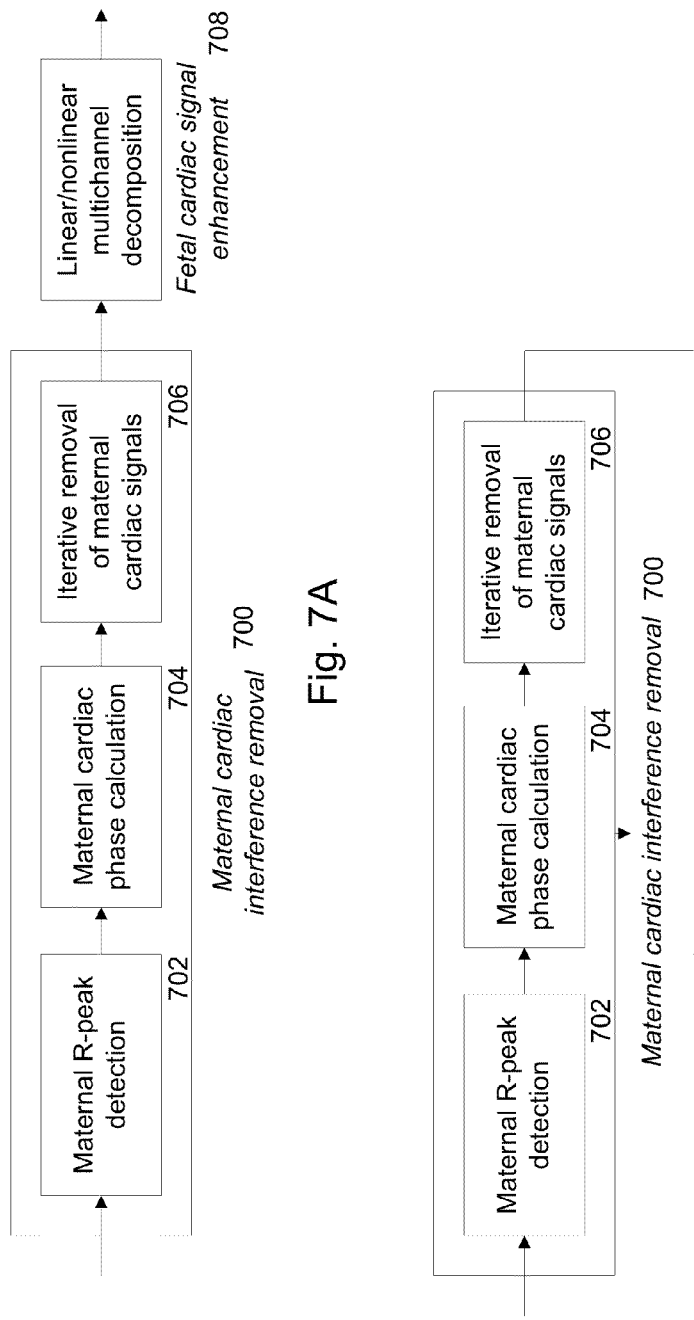
FIGS. 7A and 7B are flow charts of a scheme for extraction of a fetal cardiac waveform.

Referring to FIGS. 7A and 7B, for offline processing of batches of signals, the maternal cardiac interference is removed by a deflation procedure (step 700) including detection of the maternal R-peaks (step 702), calculation of the maternal cardiac phase signal (step 704), and iterative removal of the maternal cardiac signals (step 706). In one embodiment, the fetal cardiac signal is then enhanced (step 708) by any linear or nonlinear decomposition method. In another embodiment, the fetal cardiac signal is enhanced (step 710) by using a deflation method trained over the fetal R-peaks. That is, the fetal R-peaks are detected (step 712), the fetal cardiac phase signal is calculated (step 714), and the fetal cardiac subspace is enhanced by an iterative estimation process (step 716).

Online implementation of the deflation procedure for the extraction of fetal cardiac waveforms is similar to the offline batch method, except that the PRT transform is extracted and updated in real time using the most recent cardiac beats (for either the mother or the fetus). To implement such real time processing, the covariance matrices $C_x^{(k)}$ and $\tilde{C}_x^{(k)}$ are calculated online and updated from sliding windows containing several maternal cardiac beats (e.g., 10 beats), with 0%<n<100% of overlap (e.g., 25%<n<75%).

3 EXAMPLES

Example 1

Referring to FIG. 8A, the well-known DaISy fetal ECG dataset (De Moor B. (ed.). DAISY: Database for the Identification of Systems, Dept. of Electrical Engineering, ESAT/SISTA, K.U.Leuven, Belgium,URL: http://www.esat.kuleuven.ac.be/sista/daisy) is used to illustrate the above method. The dataset includes five maternal abdominal channels and three maternal thoracic channels recorded from the abdomen and chest of a pregnant woman at a sampling rate of 250 Hz.

Referring to FIG. 8B, the maternal components are extracted from the ECG of FIG. 8A. Specifically, by performing R-wave detection on one of the maternal thoracic channels, the maternal ECG phase $\phi_m(t)$ is determined. The time-varying maternal ECG period $\tau_t^m$ is calculated, from which the matrix $\tilde{C}_x$ and the generalized eigenmatrix B of the ($\tilde{C}_x$, $C_x$) pair are found and sorted in descending order of the eigenvalues. The resulting period components extracted from the dataset by maternal ECG beat synchronization are shown. The first component (curve 800), which corresponds to the largest eigenvalue, has the most resemblance with the maternal ECG. As the eigenvalues decrease (i.e., curves 802-814), the signals become less similar to the maternal ECG. Curves 810 and 812 are the fetal components. Because the fetal components do not resemble the maternal ECG when averaged synchronously with respect to the maternal R-peaks, the fetal components are among the last components extracted.

Referring to FIG. 8C, the fetal components are now extracted from the ECG of FIG. 8A. ECG periodicity is considered in the matrix $\tilde{C}_x$, which uses the fetal R-peaks for extraction of the time-varying fetal period $\tau_t^f$. In this example, the fetal ECG component is first extracted from the dataset of FIG. 8A by a benchmark independent component analysis method known as JADE. The extracted fetal ECG component is used for fetal R-peak detection and phase calculation. Having determined the fetal ECG phase $\phi_f(t)$, the GEVD process described above is used to extract the periodic components of the fetal ECG. The resulting periodic components are depicted in FIG. 8C, with the extracted components ranked according to their resemblance with the fetal ECG (i.e., the fetal ECG contribution reduces from top to bottom).

Referring to FIG. 8D, periodic components are extracted from the dataset using maternal and fetal ECG beat synchronization. The covariance matrix $\tilde{C}_x$ is calculated from the difference of $\tilde{C}_x^m$ and $\tilde{C}_x^f$. The periodic components are determined as described above. The first component (curve 850) includes primarily maternal ECG; the last component (curve 860) includes primarily fetal ECG. The intermediate components are mixtures of maternal and fetal components and noise.

Example 2

Figures 9E, 9F:
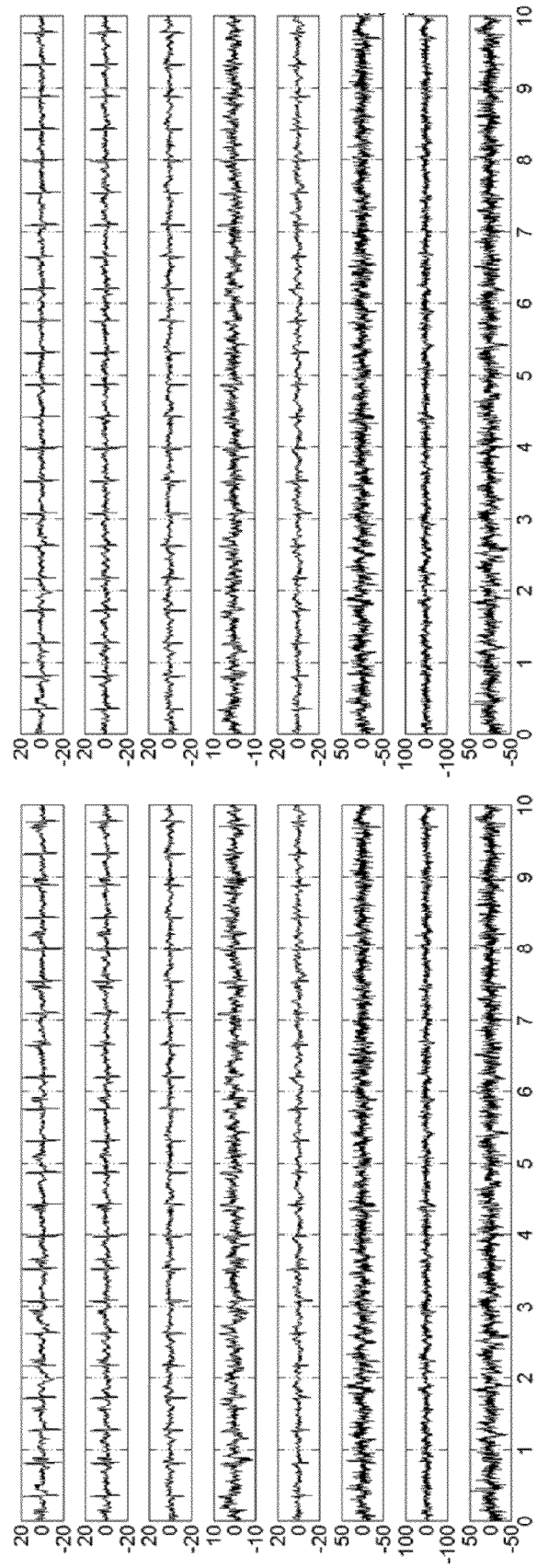
Figure 10:
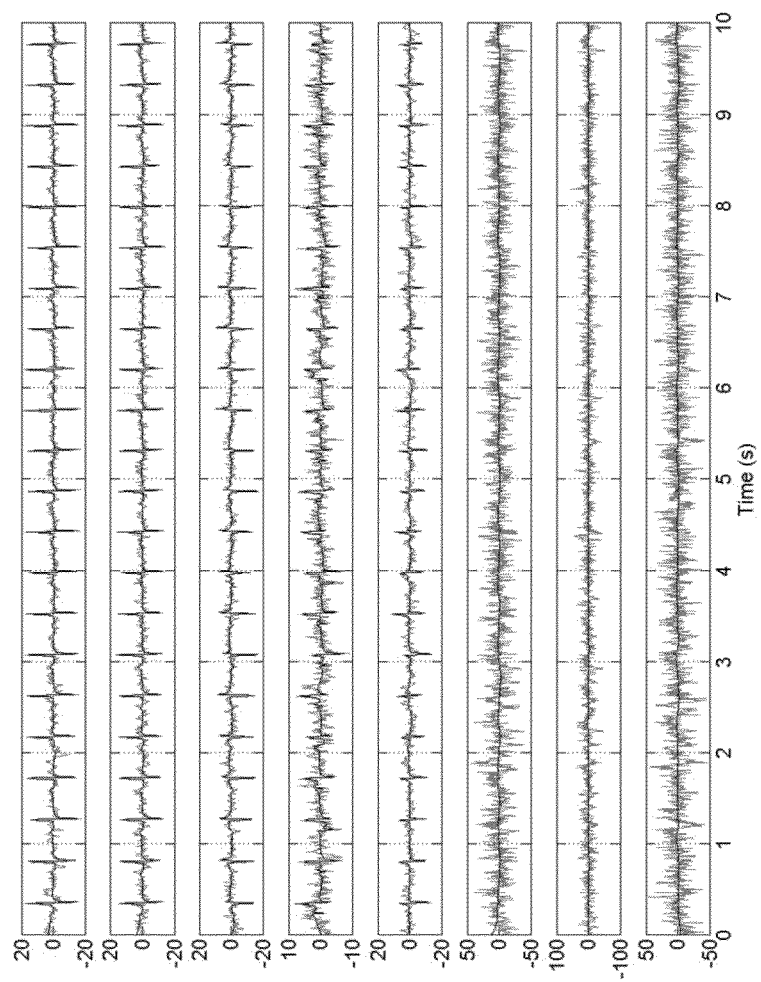
FIG. 10 is a graph showing the results of a secondary deflation step applied to the results of the last iteration shown in FIG. 9F.

Referring to FIGS. 9A-9F, the fetal components of the DaISY dataset shown in FIG. 9A are extracted and the maternal components removed by an iterative subspace removal process. Each of FIGS. 9B-9F corresponds to the result of one iteration. The periodicity measure of each iteration is listed in Table 1. The maternal ECG contaminants have been effectively reduced from the first to the last iteration. Referring to FIG. 10, a secondary deflation step was applied to the results of the last iteration of maternal ECG removal to enhance the fetal ECG. The fetal ECG signals before enhancement (gray line) and after enhancement (black line) are shown superimposed.

Example 3

Figure 11:
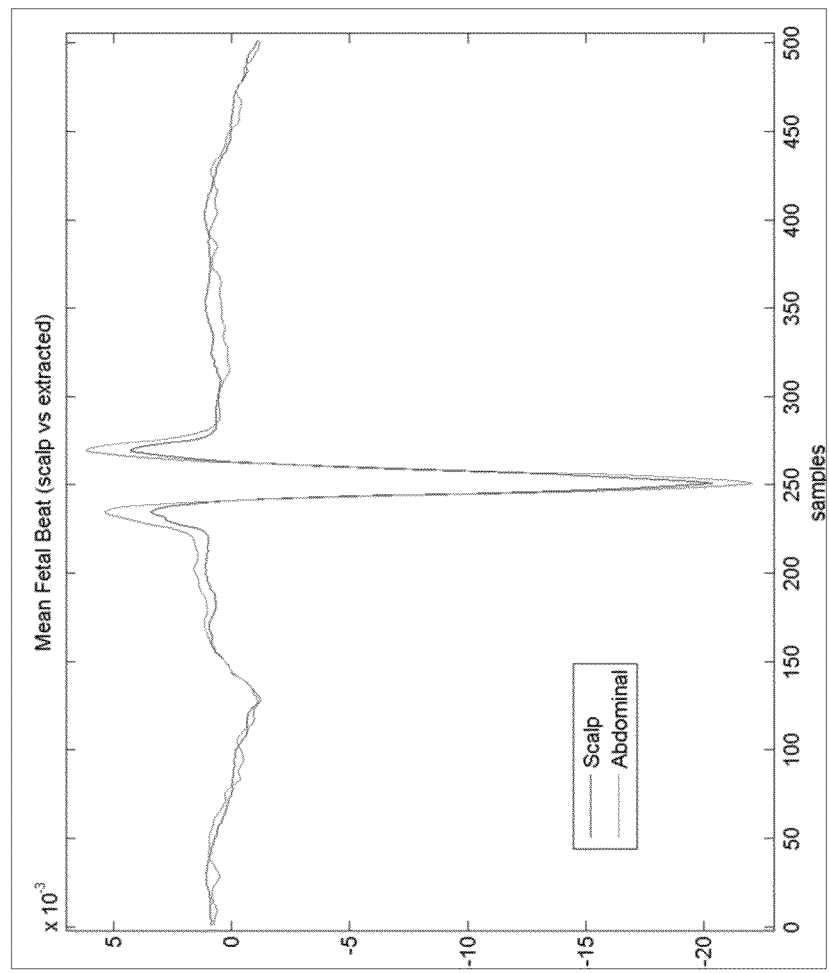
FIG. 11 is a graph comparing an averaged fetal ECG beat from a scalp electrode and an average beat extracted from an abdominal ECG during the same time period.

Referring to FIG. 11, in another example, data were acquired from 27 term laboring women who had a fetal scalp electrode (FSE) placed for a clinical indication. A total of 27 channels of abdominal data and one channel of data from a chest lead were recorded simultaneously with the FSE. The median ST level was estimated from 79 10-second segments acquired from the FSE and from preprocessed abdominal data which passed an unbiased quality test. A statistical comparison was performed to assess the accuracy of the ST deviation derived from abdominal sensors as compared to the ST deviation obtained from the "gold standard," FSE. FIG. 11 illustrates a typical fetal heart beat recorded from the scalp electrode and an extracted abdominal fetal ECG overlaid. The beat morphology is well reconstructed by the extracted signal and the extracted fetal ECG shows good fidelity with the fetal scalp ECG. In particular, the morphologies of all the clinical features are well preserved in the extracted abdominal fetal ECG, particularly the ST segment deviation. The QRS is also accurately extracted from the abdominal channels, including the R-peak height and location (relevant for respiration and heart rate (HRV) analysis, respectively). The P-wave and repolarization periods are also accurately extracted compared to the scalp electrode.

Figure 12:
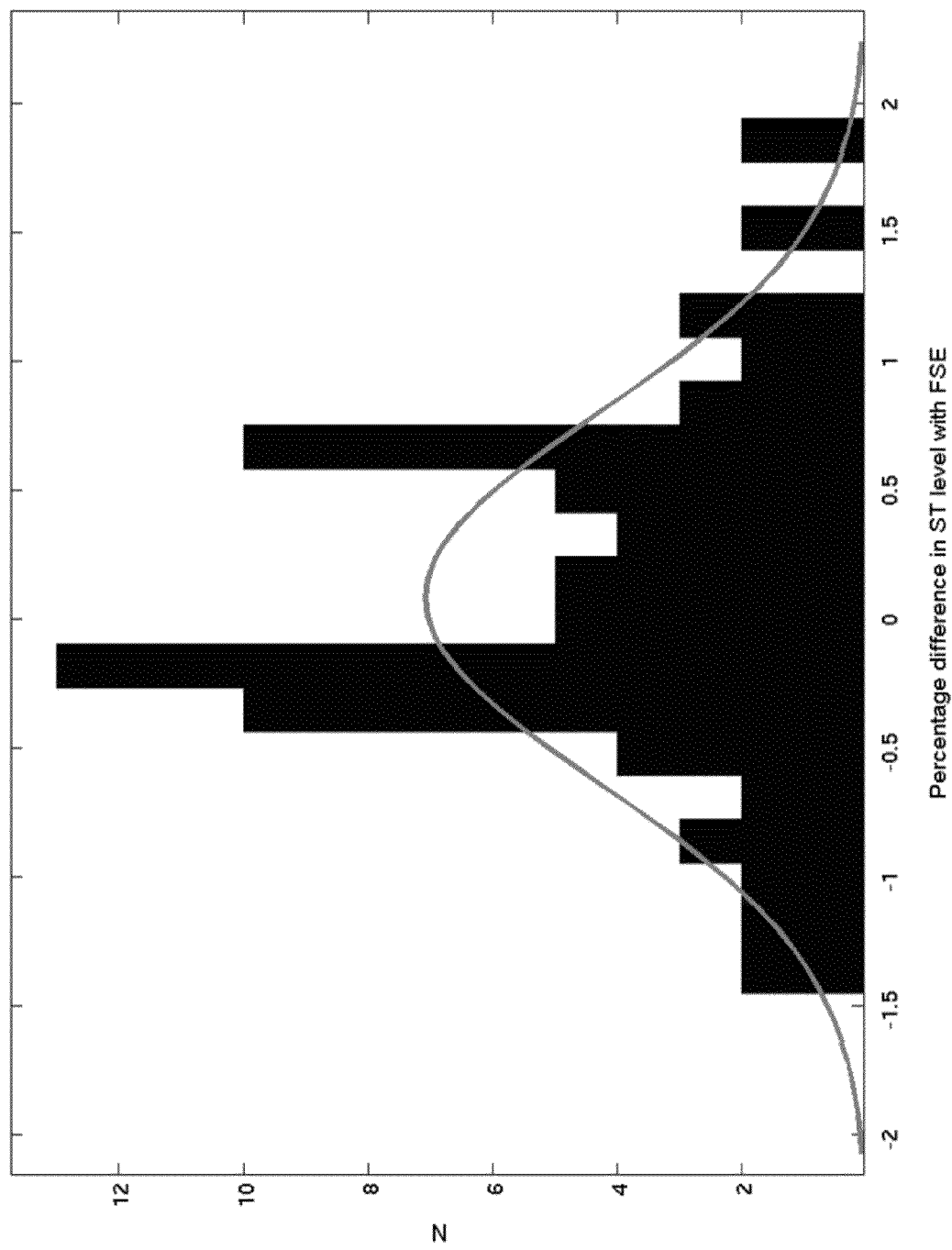
FIG. 12 is a graph showing the distribution of the difference in fetal ST deviation between ECG obtained from a fetal scalp monitor and ECG extracted from maternal abdominal signals.

When comparing the difference in the ST height above the isoelectric line between the fetal scalp electrode signal and the signal extracted from the abdominal electrodes, the root mean square error (difference) over all processed segments was determined to be on average 0.52% and the mean absolute difference was 0.29%. These units are expressed in percent relative to the R-peak height because the electromagnetic field strength is different on the abdomen and the fetal scalp. Moreover, the ST elevation for fetuses is defined in terms of its relative height compared to the R-peak. To better understand these statistics, we can compare to an adult ECG. A 0.52% deviation of an adult ST segment on a 1.5 mV amplitude beat corresponds to 0.0078 mV, which is well below the acceptable error level and would not lead to a false identification of ST elevation (or depression). FIG. 12 illustrates the distribution of the difference in ST deviation between the fetal scalp ECG and extracted abdominal fetal ECG. The gray line 1200 indicates a Gaussian fit to the empirically calculated distribution (vertical bars). Even at the extreme values of 2% deviation, the equivalent adult ST deviation would only be 0.03 mV, which is not clinically significant when compared to the amplitude of an adult ECG.

Therefore, the fetal ST deviation calculated from ECG acquired from the maternal abdomen on healthy subjects is clinically indistinguishable from ST deviations derived from the fetal scalp electrode when using the extraction method detailed in this application.

TABLE 1

Periodicity measure variation with respect to maternal ECG for each of five iterations

| Iteration | 1 | 2 | 3 | 4 | 5 |
| --- | --- | --- | --- | --- | --- |
| $\zeta(x^{(k)}(t))$ | 0.98 | 0.91 | 0.51 | 0.34 | 0.28 |

In general, the methods described above are applicable in clinical, theoretical, and experimental situations. For instance, clinical study of pathological cases is enabled. Theoretically, performance bounds for ECG processing can be calculated and theoretical aspects of the deflation method (e.g., convergence and stability) can be studied. Experimentally, fetal ECG tracking for continuous monitoring can be investigated and fetal monitoring systems can be developed.

4 IMPLEMENTATIONS

The approaches described above may be implemented in hardware, software, or using a combination of hardware and software. Hardware may include analog signal processing circuitry, digital signal processing circuitry or both. Software may include instructions stored on or transmitted over a machine readable medium. The instructions can include instructions for causing a processor (e.g., a general purpose computer processor, a digital signal processor, special purpose processor, virtual computer, a complex programmable logic device (CPLD), a field programmable gate array (FPGA), etc.) to implement the processing steps of approaches described above. The instructions can include instructions for multiple separate processors, which may be integrated into a single unit or distributed into multiple separate units.

In some implementations, a system includes signal acquisition hardware, which can include components for receiving biosignals such as ECG signals, and can include the sensors that acquire such signals, such as electrodes for placement on the maternal abdomen. In some implementations, a system includes signal presentation hardware, which can include components for providing processed biosignals for presentation or for further processing prior to analysis or presentation. In one implementation, the processed biosignals (e.g., fetal ECG) are presented on a computer generated display for monitoring by medical staff. In some instances, the processed biosignals are used to determine an orientation of the fetus and data or images representative of the fetal orientation are presented on a computer generated display. As another example, the processed biosignals may be provided to a system that analyzes extracted fetal ECG signals as described in copending U.S. Patent Pub. US2009/0259133A1, titled "FETAL ECG MONITORING." Data representative of the analysis, such as a diagnostic score related to the entropy (i.e., variability) of the processed biosignals, are presented on a computer generated display.

Although primarily described with reference to maternal ECG cancellation, the methods disclosed herein are broadly applicable to a wide range of data processing situations in which a contaminant signal is to be removed. For instance, ECG artifacts may be removed from other biosignals such as an electroencephalogram (ECG) or an electromyogram (EMG). More generally, enhancement and/or removal of pseudo-periodic signals may be applied in various areas including communication and sensor systems. As one example, communication signals that include periodic power line interference may be enhanced using the techniques described above, for example, for mitigation of pseudo-periodic interference in communication signals over powerlines.

Figure 14:
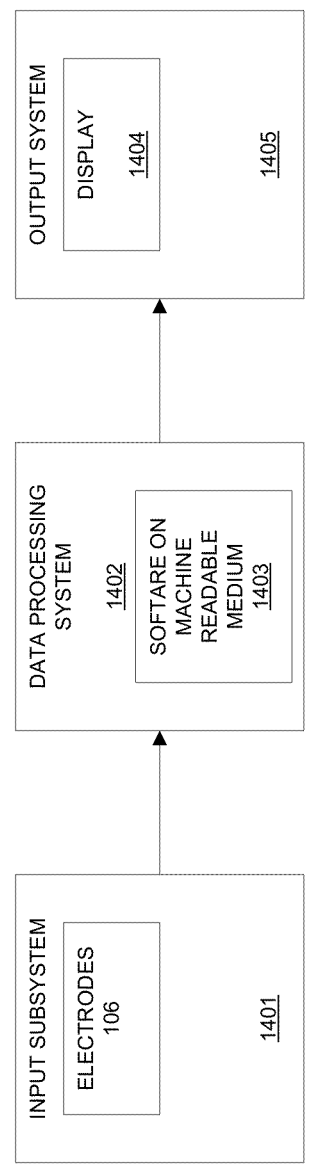
FIG. 14 is a block diagram of a cardiac monitoring system.

FIG. 14 shows a block diagram of an embodiment of a cardiac monitoring system. The system includes an input subsystem 1401, which includes the electrodes 106. A data processing system 1402 processes the accepted signals (e.g., cardiac signals). In some implementations, the data processing system includes software on a machine readable medium 1403. An output system 1405 provides information determined by from the processed signals. In some implementations, the output system includes a display 1404.

It is to be understood that the foregoing description is intended to illustrate and not to limit the scope of the invention, which includes the scope of the appended claims. Other embodiments are within the scope of the following claims, and other aspects are not necessarily represented by the following claims.

What is claimed is:

1. A method for processing an input signal that includes a pseudo-periodic signal present with another signal, the method comprising:
    accepting the input signal, the input signal being representable as a vector signal in a multidimensional vector space;
    forming a phase signal representing a time-varying periodicity of the pseudo-periodic signal;
    identifying a subspace of the vector space that exhibits correlation at the time-varying periodicity;
    forming a component of the input signal according to the identified subspace; and
    processing the input signal to either enhance or to mitigate an effect of the formed component to produce a processed signal.

2. The method of claim 1 wherein accepting the input signal comprises accepting a biosignal, the pseudo-periodic signal having a periodicity related to a periodic biological process.

3. The method of claim 2 wherein the biosignal comprises a signal acquired by sensing a signal from a human body, and wherein the periodic biological process comprises a cardiac process.

4. The method of claim 1 further comprising presenting the processed signal on a display.

5. The method of claim 1 wherein
    forming the phase representation includes identifying repetitions of a signal characteristic in the input signal;
    identifying the subspace includes determining a generalized eigenspace from a correlation of the input signal at a time varying lag determined from the phase representation and from a correlation of the input signal at zero lag;
    forming the component of the input signal according to the identified subspace includes projecting the input signal onto the eigenspace; an
    processing the input signal to either enhance or to mitigate and effect of the formed component to produce a processed signal includes at least one of adding or subtracting the projection of the signal onto the eigenspace.

* * * * *